United States Patent [19]

Murray et al.

[11] 4,077,408

[45] Mar. 7, 1978

[54] CATAMENIAL DEVICE EMPLOYING POLYMERIC CONSTRAINING MEANS

[76] Inventors: Jerome L. Murray, 652 First Ave., New York, N.Y. 10016; Frances R. Gardiner, 43 Park Rd., Sparta, N.J. 07871

[21] Appl. No.: 575,202

[22] Filed: May 7, 1975

Related U.S. Application Data

[63] Continuation-in-part of Ser. No. 436,391, Jan. 24, 1974, abandoned.

[51] Int. Cl.$^2$ ............................................. A61F 13/20
[52] U.S. Cl. ...................................................... 128/285
[58] Field of Search ............... 128/263, 270, 284, 285, 128/296; 19/144.5

[56] References Cited

U.S. PATENT DOCUMENTS

| | | | |
|---|---|---|---|
| 1,575,123 | 3/1926 | Martocci-Pisculli | 128/270 |
| 2,386,590 | 10/1945 | Calhoun | 128/270 |
| 2,808,832 | 10/1957 | Myers et al. | 128/285 |
| 3,306,966 | 2/1967 | Matejcek et al. | 128/285 |
| 3,595,236 | 7/1971 | Corrigan | 128/285 |
| 3,664,343 | 5/1972 | Assarsson | 128/285 |
| 3,690,321 | 9/1972 | Hirschman | 128/285 |

Primary Examiner—Stephen C. Pellegrino
Assistant Examiner—Henry S. Layton
Attorney, Agent, or Firm—Mel K. Silverman; David A. Jackson

[57] ABSTRACT

A catamenial device such as a tampon which comprises a segment of a rapidly re-expandable hydrophilic polymeric foam held in compression to less than 50 percent of its original dry volume and a constraining means holding said segment in compression which is adapted to provide lubrication for insertion of said segment into an animal's body cavity and to thereafter rapidly disintegrate, wherein said constraining means comprises a capsule prepared from a water-soluble alkylene oxide polymer such as poly (ethylene oxide). The devices of the present invention exhibit surprising lubricity and shelf-life, and are economically prepared.

13 Claims, 5 Drawing Figures

CATAMENIAL DEVICE EMPLOYING POLYMERIC CONSTRAINING MEANS

CROSS REFERENCE TO RELATED APPLICATIONS

This application is a continuation-in-part of co-pending Ser. No. 436,391 filed on Jan. 24, 1974, and now abandoned by the inventors herein.

BACKGROUND OF THE INVENTION

This invention generally relates to catamenial devices such as tampons and other insertable articles which are prepared from hydrophilic polymeric foam materials.

As noted in the above-identified co-pending application, catamenial devices such as tampons have been prepared from a wide variety of synthetic and naturally occuring organic materials in the form of fibers and sponge-like materials, but have all suffered from various critical defects. Generally, a device such as a tampon which is to be inserted in an easily irritable area of the body cavity must possess a refined texture and flexibility, while, at the same time, possessing a significant absorptive capacity and the ability to rapidly and uniformly re-expand in contact with moisture such as occasioned by the menstrual flow. The latter property is required because the device must assume a reduced size to facilitate its insertion.

Generally, prior art devices have lacked one or more of the above properties, as absorption is usually gained at the expense of size, and flexibility and texture are sacrificed to the ability to undergo re-expansion.

In the context of the above discussion, Applicants sought to provide a device combining all of the favorable characteristics, and, accordingly, developed a catamenial device prepared from a hydrophilic, rapidly re-expandable polymeric foam which is compressed to less than 50 percent of its dry volume and then placed within a soluble, lubricious constraining means such as a capsule. The material most often comprising the capsule of this device is a gelatin compound, which was known to possess the requisite lubricity and solubility as well as non-toxicity to living tissue.

Further experimentation conducted since the development of the above has uncovered a useful alternate material for the preparation of the constraining means which possesses all of the above properties and is easier and less expensive to employ.

SUMMARY OF THE INVENTION

In accordance with the present invention, a catamenial device is disclosed which comprises a rapidly expandable hydrophilic polymeric foam compressed and placed within a soluble lubricious constraining means, such as a capsule wherein the constraining means is prepared from a water-soluble alkylene oxide polymer. In a preferred embodiment, the polymer comprises poly (ethylene oxide) which may either be employed in sheet form or molded to the shape of a capsule having one open end. If used as a sheet, the polymer is prepared in a thickness of about 3 mils, and may be shaped into a cylindrical tube.

Catamenial devices employing the above capsules possess favorable shelf-life and lubricity on insertion into a body cavity, and are capable of rapid activation in response to moisture. In the case of tampons, the incidence of faults such as "by-pass" is virtually eliminated, as the improved expansion of the foam prevents even minor leakage from occuring.

The devices of this invention are easily and inexpensively manufactured by a variety of techniques. The capsule material withstands extended storage without collapse or deterioration.

Accordingly, it is a principal object of the present invention to prepare a catamenial device comprising a compressed hydrophilic polymeric foam constrained within a soluble container, which container possesses favorable lubricity and solubility at reduced material cost.

It is a further object of the present invention to provide a device as aforesaid wherein said container is prepared from water-soluble alkylene oxide polymer.

It is yet a further object of the present invention to provide a device as aforesaid which is easily and inexpensively manufactured and possesses extended shelf-life and structural integrity.

Other objects and advantages will be apparent to those skilled in the art from the ensuing description and accompanying drawings.

DETAILED DESCRIPTION

Figure 1:
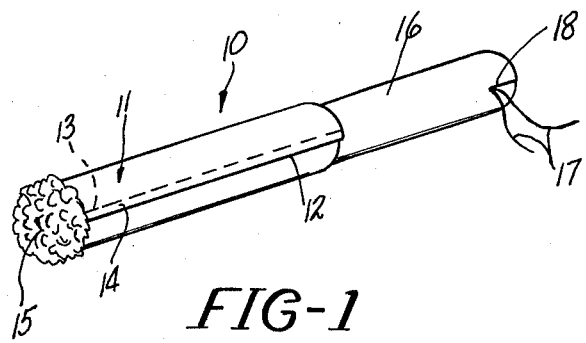
FIG. 1 is a perspective view showing a tampon prepared in accordance with the invention.

In accordance with the present invention, the foregoing objects and advantages are readily obtained.

The present invention comprises a catamenial device prepared from a rapidly re-expandable hydrophilic polymeric foam which is compressed and situated within a soluble lubricious constraining means, which comprises a capsule prepared from a watersoluble alkylene oxide polymer. Specifically, the polymer comprises poly (ethylene oxide) which may be obtained in sheet form and molded into an open-ended cylindrical container, or may be molded from starting stock into capsular configuration. The containers are prepared with a wall thickness of about 3 mils.

The preparation of the device of the present invention is generally disclosed in our parent application Ser. No. 436,391. The foams disclosed therein comprise hydrophilic polyurethane foams or hydrophilic formaldehyde polyvinylalcohol foams. It is preferred, however, that the foam be a hydrophilic polyurethane foam. A commerically available hydrophilic polyurethane foam is marketed under the tradename Acquell ® and is available from the Scott Paper Company. Ths is a polyurethane foam produced by the reaction of a polyesterdiol and tolylene diisocyanate. The polyesterdiol also contains adipic acid and block copolymers of polyoxyethylene and polyoxypropylene.

Another foam which may be used in accordance with this invention is prepared by, in a first step, forming a prepolymer by the reaction of polyethylene glycol and trimethylol propane in a mole ratio of about 2:0.125 to 2:2 respectively, followed by capping the reaction product at all hydroxy locations using tolylene diisocyanate consisting of about an 80/20 mixture of the 2,4 isomer to 2,6 isomer; and in a second step reacting 100 parts by weight of prepolymer with 30 parts by weight of water containing 5 parts by weight of a polyoxyalkylene non-ionic surfactant. A particular non-ionic surfactant which has been found useful is one commercially available under the tradename Pluronic L-64 from the Wyandotte Chemicals Corporation. Although the above comprise the preferred hydrophilic urethane foam materials, other useful hydrophilic urethane foams are produced by varying the above prepolymer to water ratio, as well as varying the water to surfactant ratio. Polymeric foams which are to be employed in the preparation of a tampon assembly should preferably possess a maximum density of about 2.5 lbs./ft.$^3$, as difficulties arise in the compression and encapsulation of foams whose density exceeds this level.

The above foams may be further modified in accordance with co-pending applications Ser. Nos. 575,356 and 575,348 filed concurrently herewith, and incorporated herein by reference, which disclose the impregnation of said foams with from 10 to 200% of their weight, of a solid, water insoluble release agent which may be respectively, either an inorganic, solid material, or a colloidal suspension of a solid, organic material. The above release agents function to keep the cell walls of the foam apart while the foam is in a compressed state and thereby enhance their re-expansion in contact with moisture.

The general preparation of the constrained device comprises the compression of the foam followed by insertion in the compressed state into a constraining means such as a capsule. Compression of the foam is usually conducted to a reduction of at least about 50% of its original dry volume, and in a preferred embodiment which is useful in tampon manufacture, the foam may be compressed from about less than 25 to about less than 10%. Any conventional type of press or device may be used. This operation may also be in combination with that of placing the compressed foam into the constraining means. As previously discussed, a preferred constraining means for a tampon is a capsule or cylinder preferably prepared from a water-soluble, lubricious, non-toxic organic material such as a poly (alkylene oxide). The foam piece, which measures about 1 × 1 × 2 inches, can be compressed and placed within the capsule or cylinder in a single step by any of the many known techniques. One useful technique is to have a cylindrical mold of the same interior diameter as that of the capsule of the sidewalls moveable to such a diameter, which cooperates with a ram which axially thrusts into the mold cavity and forces the foam into the capsule.

In the instance where the device is to function as a tampon, a draw string is attached which may be stitched into place at any time, either to the foam before encapsulation, or to the encapsulated tampon itself. Once placed in the capsule, the foam can be stored indefinitely. As discussed earlier, the capsule or cylinder readily dissolves upon contact with mositure, and the foam rapidly expands to contact the vaginal periphery.

In accordance with the present invention, and referring to FIG. 1, the device 10 is shown bearing capsule 11, which is prepared from a non-toxic, soluble film-forming material, preferably comprising poly (ethylene oxide), though, as noted earlier, other suitable poly alkylene oxides are likewise contemplated herein.

The polymers preferred in accordance with the invention, are water-soluble poly (ethylene oxide) polymers which are well known compositions whose nature and preparation are disclosed in U.S. Pat. Nos. 3,127,371; 3,214,387; 3,275,998; 3,398,199 and 3,399,149. These polymers are homopolymers of ethylene oxide and copolymers of ethylene oxide with one or more other alkylene oxides, such as propylene oxide, 1, 2 - butylene oxide, 2, 3 - butylene oxide, isobutylene oxide, styrene oxide, and the like. The polymer contains polymerized ethylene oxide in an amount sufficient to impart water solubility to it. Thus, the minimum proportion of polymerized ethylene oxide in the polymer will vary somewhat, depending upon the nature of the comonomer(s), but, in general, will be at least about 50 weight percent of ethylene oxide, and is preferably at least about 75 weight percent of polymerized ethylene oxide. Ethylene oxide homopolymer is the preferred poly (ethylene oxide) polymer.

Referring again to FIG. 1, capsule 11 is an open-ended cylindrical enclosure resembling a cigarette which is prepared from a sheet of poly (ethylene oxide) cut to predetermined dimensions. Though the thickness of the sheet may vary, a thickness of 3 mils has been found to possess a favorable combination of dry strength and rapid disintegration in contact with liquid media.

Capsule 11 may be prepared by any of several well-known methods such as, for example, wrapping the sheet material around a rod-shaped die so that longitudinal edge 12 is in overlapping relationship to the opposite edge 13 of the sheet, and then sealing the adjacent surfaces by the application of localized heat or adhesive to the overlapping margin 14 lying therebetween. If heat sealing is employed, margin 14 is preferably ⅛ inch in width to allow a sufficient weld to be made without scoring or otherwise damaging the adjacent surface.

Once formed, capsule 11 may be provided with a foam segment 15 in the manner set forth earlier, comprising the compression of the foam and its insertion into the cavity of the capsule. Naturally, the above method is merely illustrative of one procedure which may be employed, as the foam may be compressed and the sheet then wrapped therearound and secured with a suitable adhesive, etc. Once located within capsule 11, foam 15 protrudes at one end in the manner illustrated in FIG. 1, and is thus in direct registry with the vaginal canal upon insertion into the body. This configuration can be seen to provide for a rapid uptake of fluid, and corresponding expansion of the foam segment to the full diameter of the canal.

Figure 2:
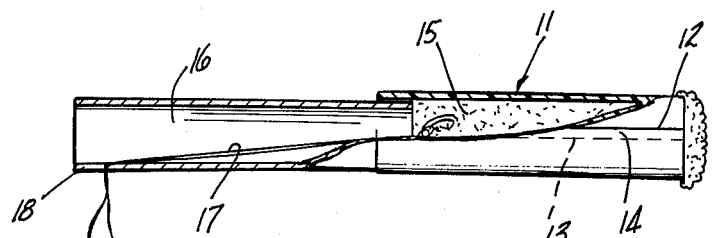
FIG. 2 is a side view partly in section showing the device of FIG. 1.

In accordance with its use as a tampon, device 10 is provided with an insertion means comprising insertion tube 16 which is shown in FIGS. 1 and 2, to be in telescopic registry with capsule 11 and abutting foam 15. Further, foam 15 is provided with a withdrawal string 17 attached thereto which extends beyond the length of tube 16. In this illustration, string 17 is secured to tube 16 by placement within slot 18 provided at the end of tube 16. Slot 18 grasps and holds string 17 and thereby prevents device 10 from dislodging prematurely from tube 16. Though the invention has been illustrated in association with a particular insertion means, it is contemplated that other conventional insertion means such as plural tubes, sticks and the like may be employed herein. Also, the device of this invention may be employed without insertion means or supports as a digitally insertable tampon.

As stated earlier, the device of the present invention may be prepared in a variety of configurations. Thus, referring to FIG. 3, a device 10' is shown which is substantially identical to the device of FIGS. 1 and 2, with the exception that the capsule 11' at the end opposite the location of string 17' has been extended and rolled or otherwise formed inward to define a blunted tip portion 19 which longitudinally constrains foam 15' between it and the abutting end of tube 16'. An opening 20 is still provided, though quite reduced in size, which enables foam 15' to effectively register with the fluids of the vaginal canal.

Figure 3:
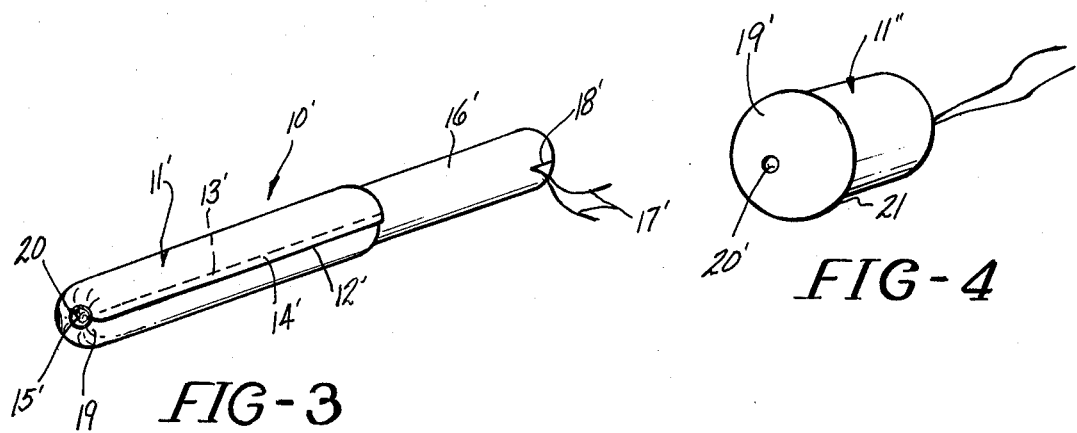
FIG. 3 is a perspective view illustrating an alternate embodiment of the invention.
Figure 4:
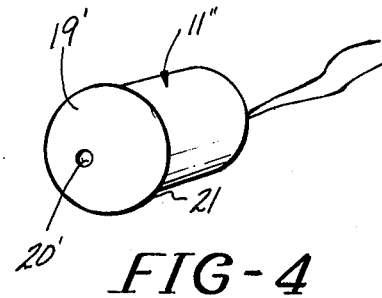
FIG. 4 is a perspective view of a tampon possessing a variant configuration from the tampon of FIG. 1.

An alternate configuration of the capsule of the invention is shown in FIG. 4, wherein capsule 11'' is shown in perspective, generally resembling the capsule of FIG. 3. Capsule 11'' differs, however, as variations in overall capsule shape are possible which are fairly within its scope. Thus, FIG. 4 discloses a capsule provided with slits 12' which varies in configuration from the capsule of FIGS. 1–3. Neck region 21 is located proximally adjacent tip portion 19' rather than distally therefrom. In this embodiment, the body of capsule 11'' is reduced in diameter over substantially its entire longitudinal dimension, and resembles a mushroom in shape. As will be seen with reference to FIG. 5, the reduced diameter of capsule 11'' over a substantial portion of its length permits it to nest deeply in an insertion device.

Figure 5:
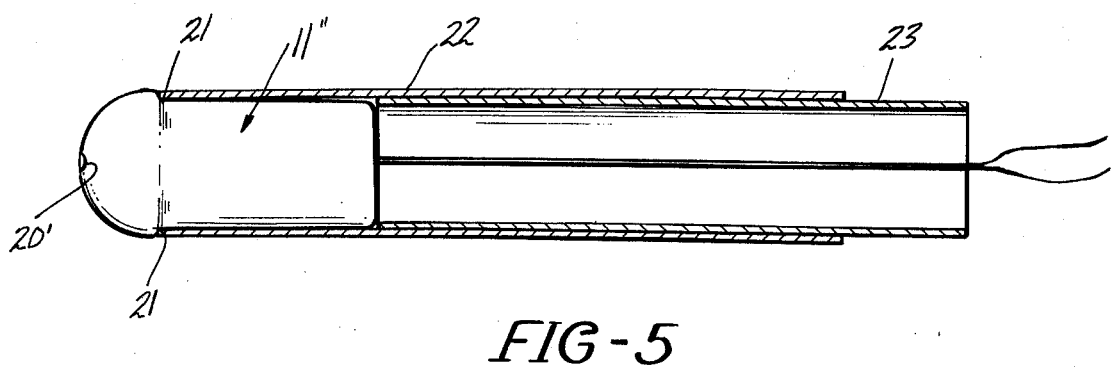
FIG. 5 is a side view partly in section showing the tampon of FIG. 4 mounted on telescoping insertion tubes.

Turning now to FIG. 5, the tampon of FIG. 4 is shown in full assembly prior to insertion, and is mounted on an insertion device comprising two telescoping tubes. Capsule 11'' is mounted within outer tube 22 which firmly grips necked region 21 and prevents accidental discharge of the tampon. Tube 23 is an ejecting tube which discharges the tampon into the vagina. These tubes may be made from a variety of materials well known for this utility in the tampon art, such as cardboard, plastic, a combination of these materials and the like.

The tampons described above may be employed as prepared or may also contain, as desired, various suitable additives such as disinfectants, perfumes, medicaments, deodorants, emollients, pigments and/or dyes. In a further embodiment, the devices of the present invention may be employed to test for the presence of various microorganisms, by the incorporation of suitable chemical indicators. Naturally, the size and shape of the tampons of this invention may vary widely to account for variations in locus of use and function.

Throughout the specification, all percentages of ingredients are expressed as percent by weight.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A catamenial device comprising:
    a segment of hydrophilic polymeric foam which is held in mechanical compression to less than 50 percent of its original dry volume said segment capable of re-expansion in the dry state; and
    an external, self-sustaining, water-soluble container within which said segment is placed subsequent to the imposition thereon of said mechanical compression, said container serving to substantially hold said segment in said compression therewithin, along the entire length of said segment, provides lubrication for insertion of said segment into an animal's body cavity and is adapted for rapid disintegration into said body cavity,
    wherein said water soluble container is prepared from a water soluble poly (alkalene oxide) polymer.

2. The device of claim 1 wherein said compressed hydrophilic foam comprises a polyurethane foam.

3. The device of claim 1 wherein said compression ranges from about less than 25 percent to about less than 10 percent of said original dry volume.

4. The device of claim 1 wherein said poly (alkylene oxide) polymer is selected from the group consisting of poly (ethylene oxide), poly (propylene oxide), poly (butylene oxide), homopolymers and copolymers thereof.

5. The device of claim 4 wherein said poly (alkylene oxide) comprises poly (ethylene oxide).

6. The device of claim 1 wherein said container comprises a capsule open at one end.

7. The device of claim 6 wherein said capsule includes a segment adjacent said open end of reduced diameter defining a shoulder about the periphery of said capsule intermediate its ends.

8. The device of claim 7 further comprising removable insertion means axially communicating with said capsule to insert said segment into said body cavity.

9. The device of claim 8 wherein said removable insertion means comprises at least one tube member and said capsule housing said segment is fitted within one end of said tube member with said shoulder abutting thereon.

10. The device of claim 1 wherein said container comprises a capsule open at both ends.

11. The device of claim 5 further comprising removable insertion means comprising telescopically received within said capsule at one end thereof, and wherein said received end of said tube member abuts said foam segment.

12. The device of claim 1 further including a withdrawal string affiexed to said segment to facilitate removal from said body cavity after use.

13. The device of claim 1 further containing an additive selected from the group consisting of deodorants, disinfectants, perfumes, emollients, medicaments, pigments, dyes and mixtures thereof.

* * * * *